US00PP11199P

United States Patent [19]

Bradford et al.

[11] Patent Number: Plant 11,199

[45] Date of Patent: Feb. 1, 2000

[54] PEACH TREE 'CORAL PRINCESS'

[76] Inventors: Lowell Glen Bradford, 12439 E. Savana Rd.; Norman G. Bradford, 11875 E. Savana Rd., both of Le Grand, Calif. 95333

[21] Appl. No.: 09/007,339

[22] Filed: Jan. 15, 1998

[51] Int. Cl.[7] ..... A01H 5/00

[52] U.S. Cl. ..... Plt./195

[58] Field of Search ..... Plt./195, 196, 190, Plt./197

[56] References Cited

U.S. PATENT DOCUMENTS

| | | | |
|---|---|---|---|
| P.P. 8,948 | 10/1994 | Bradford et al. | Plt./190 |
| P.P. 9,515 | 4/1996 | Bradford et al. | Plt./195 |
| P.P. 9,882 | 5/1997 | Zaiger et al. | Plt./195 |
| P.P. 10,190 | 1/1998 | Zaiger et al. | Plt./195 |

*Primary Examiner*—Howard J. Locker
*Assistant Examiner*—Wendy A Baker

[57] ABSTRACT

The present invention relates to a peach tree, *Prunus persica*, and more particularly to a new and distinct variety broadly characterized by a large sized, vigorous, hardy, self-fertile, productive and regular bearing tree. The fruit matures under the ecological conditions described approximately the first week in July, with first picking on Jul. 4th, 1997. The fruit is uniformly large in size, sweet and subacidic in flavor, globose in shape, clingstone in type, firm in texture, white in flesh color, and mostly red in skin color. The variety was developed as a first generation cross using Diamond Ray (U.S. Plant Pat. No. 8948) yellow flesh nectarine as the selected seed parent and an unnamed white flesh peach seedling as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of peach tree, which has been denominated varietally as 'Coral Princess'. The present variety was hybridized by us in 1992, grown as a seedling on its own roots in our greenhouse, and transplanted to a cultivated area of our experimental orchard at Bradford Farms near Le Grand, Calif. in Merced County (San Joaquin Valley). It was developed as a first generation cross using 'Diamond Ray' (U.S. Plant Pat. No. 8,948) yellow flesh nectarine as the selected seed parent and an unnamed white flesh peach as the selected pollen parent. Subsequent to origination of the present variety of peach tree, we asexually reproduced it by budding and grafting, and such reproduction of plant and fruit characteristics were true to the original plant in all respects. The reproduction of the variety included the use of Nemaguard Rootstock, the standard of the stone fruit industry in central California, upon which the present variety was compatible and true to type.

The fruit produced by the present variety is most similar to the 'White Princess' (U.S. Plant Pat. No. 9,515) white flesh peach by producing peaches that are white in flesh color, subacidic and sweet in flavor, firm in texture, and mostly red in skin color, but is distinguished therefrom and an improvement thereon by producing fruit that is clingstone instead of freestone, that is virtually free of red texture streaking, and that matures about 30 days earlier.

The present variety is similar to its selected seed parent, 'Diamond Ray' (U.S. Plant Pat. No. 8,948) yellow flesh nectarine, by abundantly producing clingstone fruit that is globose in shape, nearly full red in skin color, and matures in early July, but is distinguished therefrom and an improvement thereon by producing fruit that is subacidic instead of acidic in flavor, and that is white instead of yellow in flesh color, and that is peach instead of nectarine.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of hard eating ripe on Jul. 8, 1997. All major color code designations are by reference to the Inter-Society Color Council, National Bureau of Standards. Common color names are also used occasionally.

TREE

Size: Large, surpassing a height of 11' [3.35 meters] and a spread of 9' [2.74 meters] during the third growing season after typical dormant pruning each year.

Vigor: Vigorous, responding typically to irrigation and fertilization.

The variety grows about 3' [0.91 meters] of surplus top-growth during the spring and summer.

Growth: Spreading and dense.

Form: Vase formed.

Hardiness: Hardy with respect to central California winters.

Production: Very productive, thinning necessary.

Bearing: Regular bearer, with no alternate bearing yet observed.

Fertility: Self-fertile.

Trunk:

*Size.*—Medium, reaching a diameter of 5" [127 mm.] after the third growing season.

*Texture.*—Medium to somewhat rough.

*Bark color.*—Grayish brown [61. gy.Br].

*Lenticels.*—Numerous. Color: Strong yellowish brown [74. s.yBr]. Average size: 5/16" [7.9 mm.].

Branches:

*Size.*—Medium, typical of *Prunus persica.*

*Texture.*—Smooth on 1st year wood, increasing roughness with age.

*Color.*—lst Year Wood Topside: Light grayish red [18. l.gy.R]. 1st Year Wood Underside: Light yellow green [119. l.YG]. Older Wood: Moderate brown [58. m.Br].

*Lenticels.—Numerous. Color: Strong yellowish brown* [74. s.yBr]. Average size: 1/16" [1.6 mm.].

Leaves:

*Size.*—Medium. Average Length: 5 ½" [139.7 mm.]. Average Width: 1 7/16" [36.5 mm.].

*Thickness.*—Medium.

*Form.*—Elliptical.

*Apex.*—Acutely pointed.

*Base.*—Acute.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ⅜" [9.5 mm.]. Average Thickness: 1/16" [1.6 mm.]. Color: Moderate yellow green [120. m.YG].

*Stipules.*—Numerous, 2 per leaf, up to 6 per growing tip. Average Length: 5/16" [7.9 mm.].

*Glands.*—Numbers: 2–4 per leaf. Position: Oppositely positioned on the petiole and the base of blade. Size: Small. Form: Reniform. Color: Moderate yellow green [120. m.YG].

Flower buds:

*Hardiness.*—Hardy, with respect to central California winters.

*Diameter.*—Typically ⅜" [9.5 mm.] 1 week before bloom.

*Length.*—Typically ⅞" [22.2 mm.] 1 week before bloom.

*Form.*—Free.

*Surface.*—Pubescent.

*Color.*—Pale purplish pink [252. p.pPk].

Flowers: Perfect, complete, perigynous, usually a single pistil, typically thirty or more stamens, five sepals and petal locations alternately positioned.

*Type.*—Showy.

*Number of petals.*—Usually five, rarely double.

*Petal shape.*—Circular.

*Petal margin.*—Somewhat wavy.

*Average petal diameter.*—11/16" [17.5 mm.].

*Petal color.*—Pale pink [7. p.Pk].

*Anther color.*—Dark red [16. d.Red].

*Average pistil length.*—¾" [19.1 mm.].

*Fragrance.*—Slight to moderate.

*Average flower diameter.*—1 ¾" [44.5 mm.].

*Blooming period.*—Medium to late as compared with other peach varieties.

*Onset of bloom.*—One percent on Mar. 1, 1997.

FRUIT

Maturity when described: Firm ripe, Jul. 6, 1997.

Date of first picking: Jul. 4, 1997.

Date of last picking: Jul. 14, 1997.

Size: Uniform, large.

*Average diameter axially.*—2 ¾" [69.9 mm].

*Average traversely in suture plane.*—2 ¾" [69.9 mm].

*Typical weight.*—6.66 ounces [189 grams].

Form: Uniform, globose.

*Longitudinal section form.*—Round.

*Transverse section through diameter.*—Round.

Suture: An inconspicuous line toward the base becoming a shallow groove at the apex, slightly depressed beyond the pistil point.

Ventral surface: Rounded, slightly lipped on one side toward the middle.

Lips: Slightly unequal.

Cavity: Flaring, rounded, elongated in the suture plane, suture showing on both sides, stem markings typical.

Base: Rounded to slightly truncate.

Apex: Rounded.

Pistil Point: Apical, short, depressed within the suture.

Stem: Medium.

*Average length.*—⅜" [9.5 mm.].

*Average width.*—3/16" [4.8 mm.].

*Color.*—Moderate yellow green [120. m.YG].

Skin.

*Thickness.*—Medium.

*Texture.*—Medium.

*Tenacity.*—Tenacious to flesh.

*Tendency to crack.*—None observed.

*Color.*—Dark red [16. d.R] over a light yellowish pink [28. l.yPk] background.

Down: Scant, short, does not roll up when rubbed.

Flesh:

Color.—Yellowish white [92. White] from the skin to the stone with virtually no red bleeding or streaking.

*Amygdalin.*—Scarce.

*Juice.*—Abundant, rich.

*Texture.*—Firm, crisp.

*Fibers.*—Abundant, fine.

*Ripens.*—Earliest at the apex and along the suture.

*Flavor.*—Subacidic and sweet with 15 to 18 brix.

*Aroma.*—Wanting.

*Eating quality.*—Very good.

STONE

Type: Clingstone.

Form: Elliptical.

Base: Straight.

Apex: Acuminate.

Sides: Slightly unequal.

Surface: Irregularly furrowed toward the apex and pitted toward the base.

Ridges: Jagged toward the base.

Color: Light yellowish brown [76. l.yBr].

Pit wall ¼" [6.4 mm.] thick.

Tendency to split: None observed.

Kernel:

*Form.*—Oval.

*Taste.*—Very bitter.

*Viable.*—Yes.

*Average width.*—7/16" [11.1 mm.].

*Average length.*—¾" [19.1 mm.].

*Color.*—Moderate orange yellow [71. m.OY] with moderate yellowish brown [77. m.yBr] veining.

*Amygdalint.*—Abundant.

USE

Market: Fresh and long distance shipping.

Keeping Quality: Fruit quality observed to remain in good condition in excess of 17 days in standard cold room at 36° Fahrenheit [2° Celsius].

Shipping quality: Excellent.

Resistance insects: No unusual susceptibilities noted.

Resistance to diseases: No unusual susceptibilities noted.

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to the 'White Princess ' (U.S. Plant Pat. No. 9,515) white flesh peach by producing peaches that are white in flesh color, subacidic and sweet in flavor, firm in texture, and mostly red in skin color, but is distinguished therefrom and an improvement thereon by producing fruit that is clingstone instead of freestone, that is virtually free of red texture streaking, and that matures about 30 days earlier.

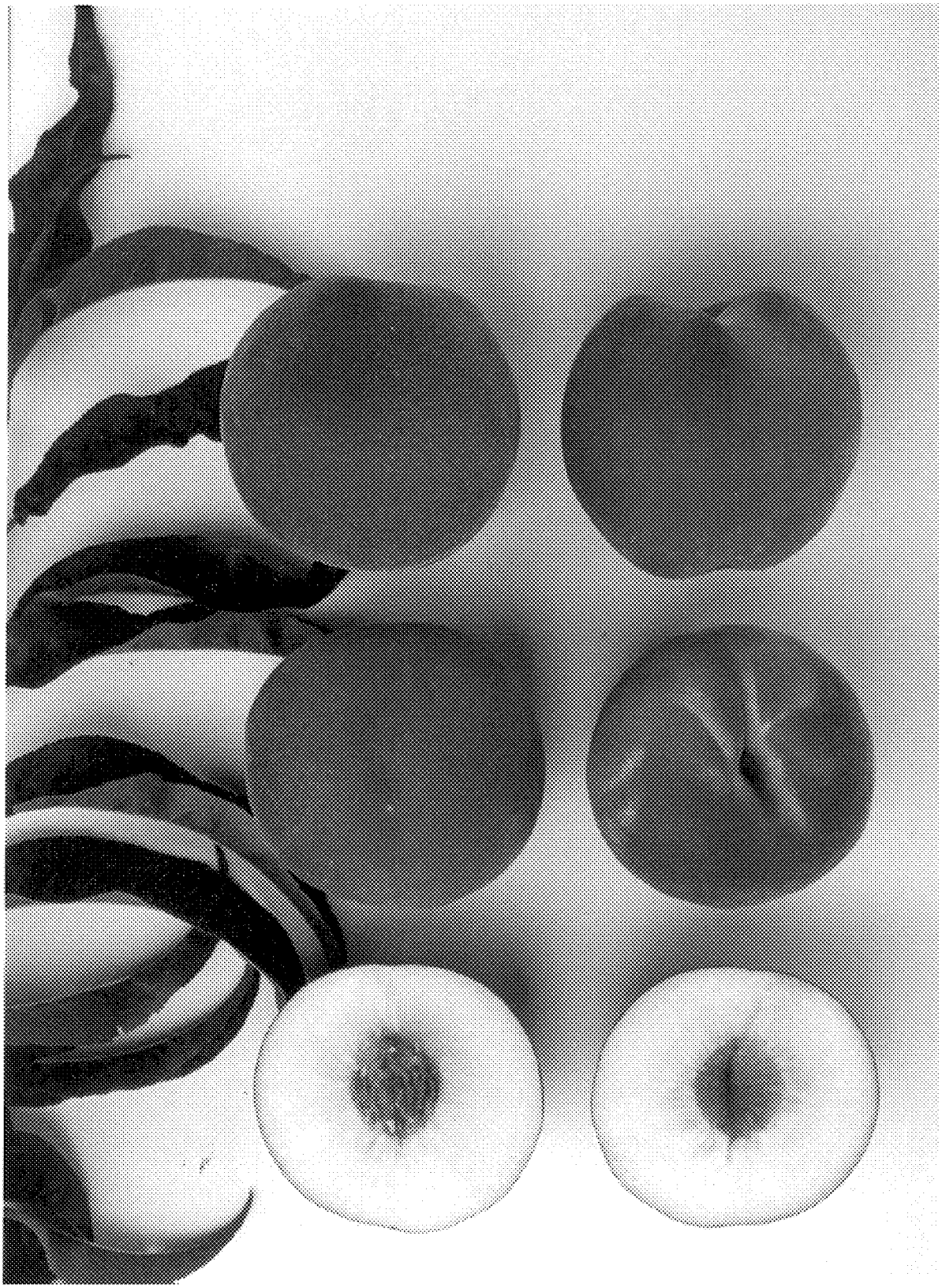

* * * * *